(12) United States Patent
Frank et al.

(10) Patent No.: US 6,309,651 B1
(45) Date of Patent: Oct. 30, 2001

(54) METHOD OF AND COMPOSITIONS FOR IMMUNIZATION WITH THE PSEUDOMONAS V ANTIGEN

(75) Inventors: Dara W. Frank, West Allis, WI (US); Timothy L. Yahr, Hanover, NH (US); Teiji Sawa; Jeanine Wiener-Kronish, both of San Francisco, CA (US)

(73) Assignees: MCW Research Foundation, Milwaukee, WI (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/448,339

(22) Filed: Nov. 23, 1999

Related U.S. Application Data (60) Provisional application No. 60/109,952, filed on Nov. 25, 1998, and provisional application No. 60/126,794, filed on Mar. 30, 1999.

(51) Int. Cl.[7] .................................................. A61K 39/08
(52) U.S. Cl. .................... 424/260.1; 424/200.1; 530/350
(58) Field of Search ............... 424/260.1, 200.1; 435/69.1, 69.3, 71.1; 530/350

(56) References Cited

U.S. PATENT DOCUMENTS 5,599,665   2/1997   Barbieri et al. .

OTHER PUBLICATIONS

Pullen et al. Infection Immunity. Feb. 1998. 66(2): 521–7, Feb. 1998.*

Frank, D. Molec. Microbiol. 1997. 26(4): 621–9, 1997.*

G.W. Anderson, Jr., et al., "Recombiant V Antigen Protects Mice aganist Pneumonic and Bubonic Plague Caused by F1–Capsule–Positive and –Negative Strains of *Yersinia pestis*," *Infect. Immun.* 64(11):4580–4585, 1996.

H. Hahn, et al., "Pilin–Based Anti–Pseudomonas Vaciens: Latest Developments and Perspectives," *Behring Inst. Mitt.* 98:315–325, 1997.

T. Sawa, et al., "Active and Passive Immunization with the Pseudomonas V Antigen Protects against Type III Intoxication and Lung Injury," *Nat. Med.* 5(4):392–398, 1999.

T.L. Yahr, et al., "Identification of Type III Secreted Products of the *Pseudomonas aeruginosa* Exoenzyme S Regulon,"*J. Bacteriol.* 179(22):7165–7168, 1997.

* cited by examiner

*Primary Examiner*—Jennifer E. Graser
(74) *Attorney, Agent, or Firm*—Quarles & Brady LLP (57) ABSTRACT

A method of inhibiting, moderating or diagnosing *Pseudomonas aeruginosa* infection is disclosed. In one embodiment, this method comprises inoculating a patient with an effective amount of PcrV antigen.

4 Claims, 5 Drawing Sheets

METHOD OF AND COMPOSITIONS FOR IMMUNIZATION WITH THE PSEUDOMONAS V ANTIGEN

CROSS-REFERENCE TO RELATED APPLICATION

This application claims priority to U.S. Ser. No. 60/109,952, filed Nov. 25, 1998 and U.S. Ser. No. 60/126,794, filed Mar. 30, 1999, both of which are incorporated by reference herein.

STATEMENT REGARDING FEDERALLY SPONSORED RESEARCH OR DEVELOPMENT

This invention was made with United States government support awarded by the following agencies: NIH/NIADA Grant Nos. R01 AI31665-08, K04 AI01289-04 and R01 HL59239-02. The United States has certain rights in this invention.

BACKGROUND OF THE INVENTION

*Pseudomonas aeruginosa* is an opportunistic bacterial pathogen that is capable of causing fatal acute lung infections in critically ill individuals (1). The ability of the bacterium to damage the lung epithelium has been linked with the expression of toxins that are directly injected into eukaryotic cells via a type III-mediated secretion and translocation mechanism (2, 3).

The proteins encoded by the *P. aeruginosa* type III secretion and translocation apparatus demonstrate a high level of amino acid identity with members of the Yersinia Yop regulon (4–6). Of all the type III systems discovered in Gram-negative bacteria, only *P. aeruginosa* possesses a homologue to the Yersinia V antigen, PcrV (see 6 for review of type III systems). Homologous proteins to the secretion and translocation apparatus are encoded by both plant and animal pathogenic bacteria. These organisms include human pathogens such as *Salmonella typhimurium, Shigella flexneri*, Enteropathogenic *E. coli, Chlamydia* spp., and plant pathogens such as *Xanthamonas campestris, Pseudomonas syringae, Erwinia amylovora* and *Ralstonia solanacearum*. However, only *P. aeruginosa* and Yersinia encode the V antigen.

Yahr, et al., 1997, discloses the sequence of the operon encoding PcrV and compares the sequence to the LcrV protein. Thus, the amino acid sequence of PcrV is known and is available under accession number AF010149 of GenBank.

SUMMARY OF THE INVENTION

The present invention involves methods and compositions developed from our observation that the Pseudomonas V antigen can be used to protect animals from a lethal lung infection.

In one embodiment, the present invention is a method of inhibiting Pseudomonas infection comprising inoculating a patient with an effective amount of PcrV antigen. In another embodiment, DNA encoding PcrV is used as a gene vaccine.

In one preferred embodiment, the antigen is expressed as a recombinant protein and used to immunize patients at risk.

Preferably, the patient is completely protected from infection.

In another embodiment, the DNA encoding PcrV (called pcrv) or a DNA fragment may be used diagnostically to detect *P. aeruginosa* infection.

In another embodiment, the recombinant protein (rPcrV) is used diagnostically to detect antibodies from patients. Patient antibody response to PcrV may be associated with prognosis. Therefore, in this embodiment the recombinant protein is used as a prognostic indicator by measuring the patient's antibody titer.

The present invention also provides a method for inhibiting a Pseudomonas infection in an individual by contacting the individual with an effective amount of a PcrV inhibitor, in particular with a PcrV antibody, antibody derivative or fragment, or antibody mimic. PcrV antibodies, antibody derivatives and antibody fragments are also provided.

It is an object of the present invention to actively and passively immunize a patient against Pseudomonas infection.

It is another object of the present invention to diagnostically detect the *P. aeruginosa* infection.

It is another object of the present invention to diagnostically detect antibodies from Pseudomonas patients.

Other objects, features and advantages of the present invention will become apparent to one of skill in the art after review of the specification, claims and drawings.

DESCRIPTION OF THE INVENTION

We disclose herein that PcrV has a novel regulatory effect on expression of the type III secreted products, is involved in the translocation of type III toxins, and is the first antigen that protects against lung injury induced by *P. aeruginosa* infection. Vaccination against PcrV prior to the airspace instillation of anti-PcrV IgG not only ensured the survival of challenged animals but also decreased lung inflammation and injury caused by the bacteria.

LcrV, or the V antigen, is a multifunctional protein that regulates secretion/translocation of the Yop effector proteins and plays an extracellular role in pathogenesis by altering the host cytokine response to Yersinia infection (7–11). The only known homologue of this critical pathogenic factor is an extracellular protein encoded by *P. aeruginosa*, termed PcrV.

One embodiment of the present invention is a method of moderating or inhibiting a Pseudomonas infection by immunizing a patient with an effective amount of the PcrV antigen. By "effective amount" we mean an amount of PcrV antigen effective to show some moderation or inhibition of Pseudomonas infection as compared to control subjects or animals who have not been treated with the antigen.

By "moderating" we mean that infection is inhibited by at least fifty percent compared to a non-immunized animal. Preferably, infection is completely prevented. A quantitative assessment of infection would preferably include the examination of the amount of bacteria in the bloodstream or pleural fluids and/or an examination of lung injury parameters. For example, the absence of bacteria in the blood stream or pleural fluids would indicate prevention of infection. A reduction in lung injury parameters would indicate that infection is moderated.

Infection could be quantitatively assessed by several other clinical indicators, including the reduction of bacterial load in the sputum, blood or pleural fluids, reduction in the size of the infiltrate, oxygenation improvement, reduction in the length of time on mechanical ventilation, reduction in fever and reduction in white blood cell count.

By "PcrV antigen" we mean that portion or fragment of the PcrV protein that is necessary to invoke an immune response which prevents or moderates infection. Currently, we have used the full-length PcrV protein as an antigen to induce protection. However, one of skill in the art can map the protective epitope on the molecule. For example, we will be producing monoclonal antibodies and screening them for the antibodies that prevent cytotoxicity in tissue culture. Antibodies that prevent cytotoxicity will be tested in the acute lung infection model for passive protection against infection. Monoclonal antibodies generally recognize a small region of amino acids and when the amino acids are contiguous, the epitope can be defined to as few as 6–9 amino acids. To define the epitope, monoclonal antibodies that protect against infection and cytotoxicity will be tested for binding to progressively smaller forms of recombinant PcrV. (By "recombinant PcrV" or "rPcrV" we mean the protein produced from a PcrV gene that has been placed in a non-native host.) This should localize the region. At this point we will chemically synthesize amino acid stretches to define the epitope. These chemically synthesized epitopes can be attached to carrier molecules and used for immunization to determine if protection is achieved. Alternatively, we can construct different clones of PcrV, produce and purify recombinant proteins, and test these antigens in immunization and challenge experiments.

Based on mapping studies performed with PcrV, we predict that the epitope lies between amino acids 113 and 245.

Figure 1:
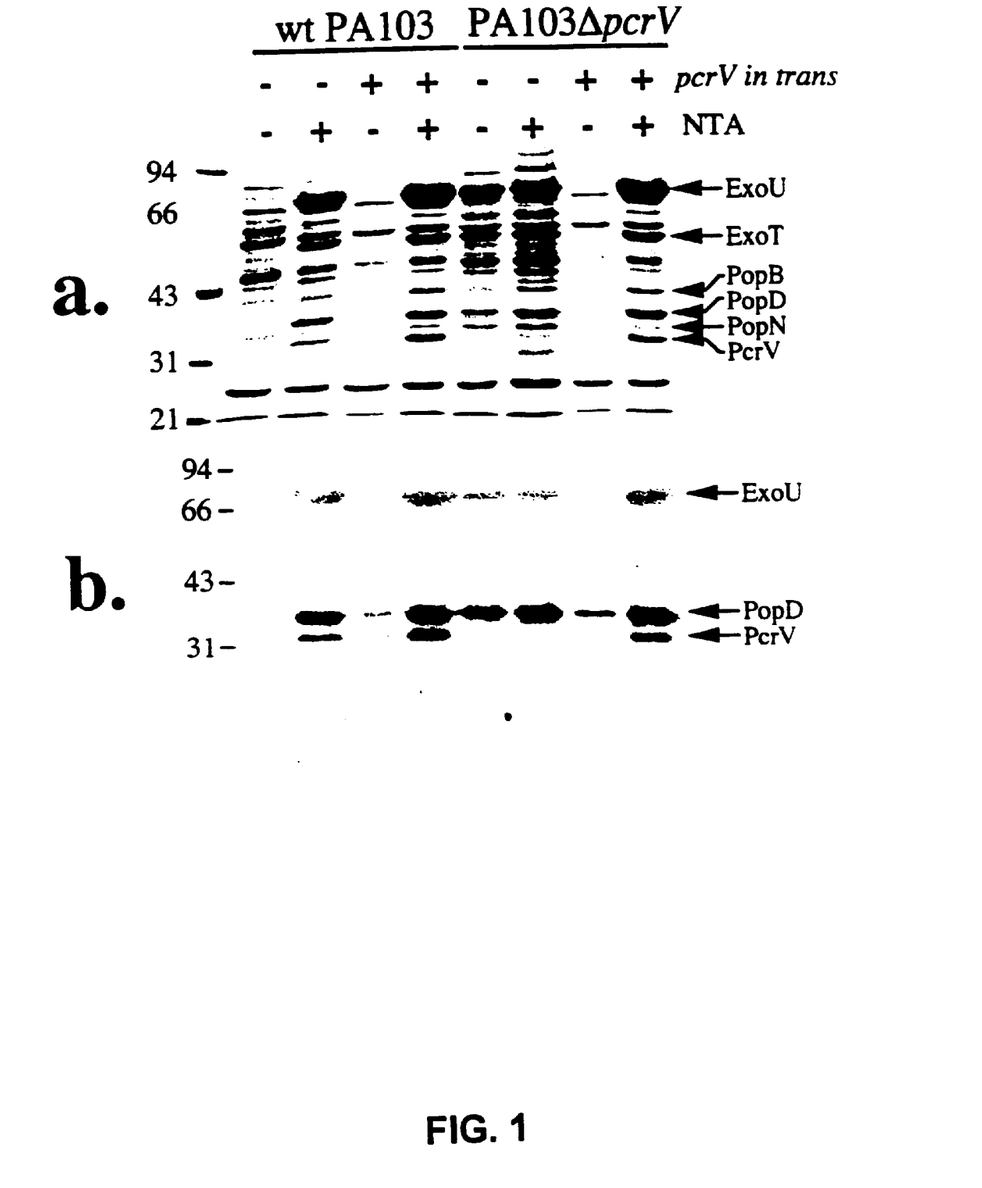
FIGS. 1A and 1B are a stained gel (FIG. 1A) and Western blot (FIG. 1B) illustrating the phenotypic analysis of PA103ΔpcrV.

The PcrV antigen may be most easily obtained by the method we used, a commercially available bacterial expression plasmid called pet16b from Novagen. The pcrv gene was first cloned from the *P. aeruginosa* chromosome as part of an operon. The coding region was amplified and inserted into two different vectors. One vector is for expression from *P. aeruginosa* as shown in FIG. 1. This is a vector from Herbert Schweizer (reference 19) which we modified to contain an appropriate promoter sequence such that PcrV expression is coordinately regulated with the rest of the delivery and intoxication apparatus of the bacterium. The second plasmid, pET16b, is for expression and purification purposes from *E. coli*.

The advantage of this system is that we do not have to worry about contaminating *P. aeruginosa* proteins, the protein is produced in great abundance, and there is a one-step purification process. In this situation the PcrV coding region is amplified to be cloned in frame with a histidine tag provided on the pET16b vector. The multiple histidine residues fused to the amino terminus of PcrV allow affinity chromatography using a nickel-NTA column. Therefore, a preferable PcrV antigen is a recombinant version of the natural PcrV protein.

In another embodiment, human or humanized monoclonal or polyclonal antibodies to PcrV are administered to prevent or treat infections with *P. aeruginosa*. In patients at high risk for *P. aeruginosa* infection, antibodies could be administered for prevention of infection. In addition, antibodies may be administered after the onset of infection to treat the infection. In this case, antibodies can be administered alone or in combination with antibiotics. Administration of antibodies in conjunction with antibiotics may allow the administration of shorter courses or lower doses of antibiotics, thereby decreasing the risk of emergence of antibiotic-resistant organisms.

We envision at least three types of hypothetical patients: (1) A healthy individual at risk of serious injury or burn (fire fighter, military personnel, police) would be immunized with the vaccine by a methodology (either injection or intranasal) that would give long-lived protection. A booster would be given on admission (intramuscular injection) to the hospital after injury. (2) A patient who is being subjected to mechanical ventilation. (3) A patient who has been genetically diagnosed with cystic fibrosis.

Immunization may be done systemically or intranasally. Immunization of these individuals would preferably start during normal vaccination procedures for other childhood diseases. We would predict long-lived protection with booster doses probably around ages 5 and 10.

In another embodiment, one would use DNA encoding the PcrV protein or the complement of this DNA to diagnostically detect *P. aeruginosa* infection. One would obtain the DNA sequence of the PcrV antigen at GenBank AF010149. The coding region for PcrV is at nucleotides 626–1510. One may also choose to use a fragment of this coding region or complement of this fragment. A successful probe is one that will hybridize specifically to the PcrV DNA and not to other regions.

One would preferably use a hybridization probe of at least 40 continuous nucleotides within the antigen sequence or two primers of at least 25 continuous nucleotides within the sequence. One skilled in the art would appreciate that many standard forms of nucleic acid diagnostic techniques would be suitable, for example, hybridization of the single-stranded 40 nucleotide probe to DNA or RNA extracted from a patient's sputum. In another example, patient's sputum would be used as a source for bacterial DNA or RNA to serve as a template for the PCR or RT-PCR reaction, respectively.

One would also determine *Pseudomonas aeruginosa* infection in an individual by contacting a sample obtained from the individual with an antibody specific for PcrV and correlating enhanced antibody binding as compared with a control sample with *Pseudomonas aeruginosa* infection in the individual.

In an additional embodiment, the DNA encoding PcrV is used as a gene vaccine using standard molecular biological methods. For example, one could review the following references for techniques known to those of skill in the art: Davis, H. L., et al., "DNA vaccine for hepatitis B: Evidence for immunogenicity in chimpanzees and comparison with other vaccines," *Proc. Natl. Acad. Sci.* 93:7213–7218, 1996; Barry, M. A., et al., "Protection against mycoplasma infection using expression-library immunization," *Nature*

377:632–635, 1995; Xiang, Z. Q., et al., "Immune responses to nucleic acid vaccines to rabies virus," *Virology* 209:569–579, 1995. By "effective amount" of a gene vaccine, we mean an amount of vaccine effective to moderate or eliminate Pseudomonas infection or Pseudomonas infection symptoms.

The protein or antigen could also be used diagnostically to detect antibodies in patients and, thus, predict the patient's infection status. One would preferably contact a sample obtained from an individual suspected of Pseudomonas infection with the PcrV protein or fragment thereof and detect protein/antibody binding. One would then correlate enhanced antibody binding (as compared with a control sample) with *Pseudomonas aeruginosa* infection in the individual.

One could also use the PcrV antibody or antibody fragments therapeutically. Once the antibody is safe for human use, one could: (a) administer it systemically and (b) administer it into the lungs as either a preventative treatment or as a therapy. In order to use the PcrV antibody in humans, the antibody is preferably "humanized". In general, once the monoclonal antibody is obtained the heavy and light chain variable regions are cloned. These cloned fragments are then inserted into a human antibody backbone (constant regions). Thus, we can control the class of antibody (IgG, IgA, etc.) in addition to providing the binding specificity.

For use in the present invention, the PcrV antibody may be a monoclonal antibody or polyclonal. The antibodies may be human or humanized, particularly for therpuetic applications. Antibody fragments or derivatives, such as an Fab, $F(ab')_2$ or Fv, may also be used. Single-chain antibodies, for example as described in Huston, et al. (*Int. Rev. Immunol.* 10:195–217, 1993) may also find use in the methods described herein. By "effective amount" of the PcrV antibody or antibody fragment we mean an amount sufficient to moderate or eliminate Pseudomonas infection or infection symptoms.

In addition to PcrV antibodies and antibody fragments, small molecule peptidomimetics or non-peptide mimetics can be designed to mimic the action of the PcrV antibodies in inhibiting or modulating Pseudomonas infection, presumably by interfering with the action of PcrV. Methods for designing such small molecule mimics are well known (see, for example, Ripka and Rich, Curr. *Opin. Chem. Biol.* 2:441–452, 1998; Huang, et al., *Biopolymers* 43:367–382, 1997; al-Obeidi, et al., Mol. *Biotechnol.* 9:205–223, 1998). Small molecule inhibitors that are designed based on the PcrV antibody may be screened for the ability to interfere with the PcrV—PcrV antibody binding interaction. Candidate small molecules exhibiting activity in such an assay may be optimized by methods that are well known in the art, including for example, in vitro screening assays, and further refined in in vivo assays for inhibition or modulation of Pseudomonas infection by any of the methods described herein or as are well known in the art. Such small molecule inhibitors of PcrV action should be useful in the present method for inhibiting or modulating a Pseudomonas infection.

In another aspect of the present invention, PcrV protein may be used to identify a PcrV receptor which may be present in the host cells, particularly in human cells, more particularly in human epithelial cells or macrophages. Identification of a PcrV receptor allows for the screening of small molecule libraries, for example combinatorial libraries, for candidates that interfere with PcrV binding. Such molecules may also be useful in a method to inhibit or modulate a Pseudomonas infection.

Our first attempts at receptor identification will be to use PcrV in pull-down experiments. PcrV will be fused to glutathione S-transferase (GST) and attached to column matrix for affinity chromatography of solubilized cellular extracts. Proteins binding specifically to PcrV will be eluted and subjected to amino terminal sequencing for identification. In parallel experiments PcrV will be subjected to yeast two-hybrid analysis. In this case PcrV is fused in frame with the DNA binding domain of Ga14. Once the clone is obtained it will be transformed into a suitable yeast host strain. The yeast strain containing the Ga14 PcrV construct will be transformed with a Hela cell cDNA bank cloned in frame with the Ga14 activation domain. Double transformants that complement the ability to utilize histidine and produce beta galactosidase (proteins that interact with PcrV) will be analyzed genetically and at the nucleotide sequence level. In case the receptor is a cellular glycolipid we will utilize an overlay technique where glycolipids are separated by thin-layer chromatography and then probed with radio-labeled bacteria. The binding to specific components will be monitored by autoradiography. Similarly, epithelial and macrophage proteins will be separated by SDS-PAGE, blotted onto nitrocellulose and overlaid with radiolabeled bacteria or labeled PcrV. Again, the protein components to which the bacteria bind are then identified by autoradiography.

Pseudomonas species are known to infect a wide spectrum of hosts within the animal kingdom and even within the plant kingdom. As will be apparent to one of ordinary skill in the art, the compositions and methods disclosed herein may have use across a wide range of organisms in inhibiting or modulating diseases or conditions resulting from infection by a Pseudomonas species. The compositions and methods of the present invention are described herein particularly for application to *Pseudomonas aeruginosa* but it is well within the competence of one of ordinary skill in the art to apply the methods taught herein to other species.

EXAMPLES

1. Role of PcrV in Cytotoxicity

To determine the role of PcrV in type III-mediated regulation/secretion, we constructed a nonpolar allele of PcrV and used the construct to replace the wild-type allele in *P. aeruginosa* strain PA103, a strain that is highly cytotoxic in vitro (3) and causes lung epithelial damage in vivo (12, 13). Cytotoxicity and lung injury are due to the production of a specific cytotoxin, ExoU (3).

PA103ΔpcrV was characterized by the expression of several extracellular products that are secreted by the *P. aeruginosa* type III system which include the ExoU cytotoxin (3), PcrV (5), and a protein required for the translocation of toxins, PopD (14). SDS-polyacrylamide gel electrophoresis of concentrated culture supernatants indicated that the parental strain, PA103 is induced for production and secretion of the type III proteins by growth in medium containing a chelator of calcium, nitrilotriacetic acid (NTA) (FIG. 1). When an expression clone encoding PcrV was provided in trans in the parental strain, extracellular protein production in response to the presence or absence of NTA is normal. PA103ΔpcrV exhibits a calcium blind phenotype; extracellular protein production is strongly induced in both the presence and absence of NTA. These results suggest that the secretory system is fully functional but deregulated. This deregulated phenotype is in contrast to the calcium independent phenotype reported for an LcrV defective strain which fails to produce the extracellular Yops, grows at 37°

C. regardless of the presence or absence of calcium, and shows only partial induction of the Yops (7). Complementing PA103ΔpcrV with a clone expressing wild-type PcrV restored normal regulation of extracellular protein production in response to NTA induction.

To test the contribution of PcrV to *P. aeruginosa* pathogenesis, two infection models were used. In an in vitro model the parental and several mutant derivative strains were compared for their ability to cause cytotoxicity in a CHO cell infection assay (3). The negative controls in this experiment included PA103popD::Ω, which has been previously shown to be defective in the translocation of type III virulence determinants (14) and PA103ΔexoU, which is non-cytotoxic due to the absence of ExoU production (3, 15).

After a 3 hour infection, CHO cells were unable to exclude trypan blue with the wild-type and ΔpcrV strain complemented with a plasmid construct expressing PcrV. Staining did not occur when CHO cells were infected with the negative control strains or with PA103ΔpcrV (data not shown). These results suggest that PcrV expression is required for cytotoxicity. Purified recombinant PcrV was not cytotoxic when added exogenously to tissue culture cells. Since secretion of the type III proteins required for translocation was unaffected by the deletion of pcrv (FIG. 1A and B), PA103ΔpcrV appears to be defective in ExoU translocation.

FIGS. 1A and 1B are a stained gel (FIG. 1A) and Western blot (FIG. 1B) illustrating the phenotypic analysis of PA103ΔpcrV. The parental and Δpcrv derivatives, with and without a plasmid expressing PcrV in trans, were grown in the absence or presence of the inducer of type III secretion in *P. aeruginosa*, nitrilotriacetic acid (NTA). The extracellular protein profile (FIG. 1A) was analyzed on a SDS-polyacrylamide gel (10%) stained with Coomassie blue. The migration of the *P. aeruginosa*-encoded type III proteins is indicated to the left and the migration of molecular weight markers is indicated on the right. FIG. 1B is a Western blot of a duplicate gel using antibodies specific for ExoU, PcrV, and PopD and $^{125}$I-Protein A to detect bound IgG.

Figure 2:
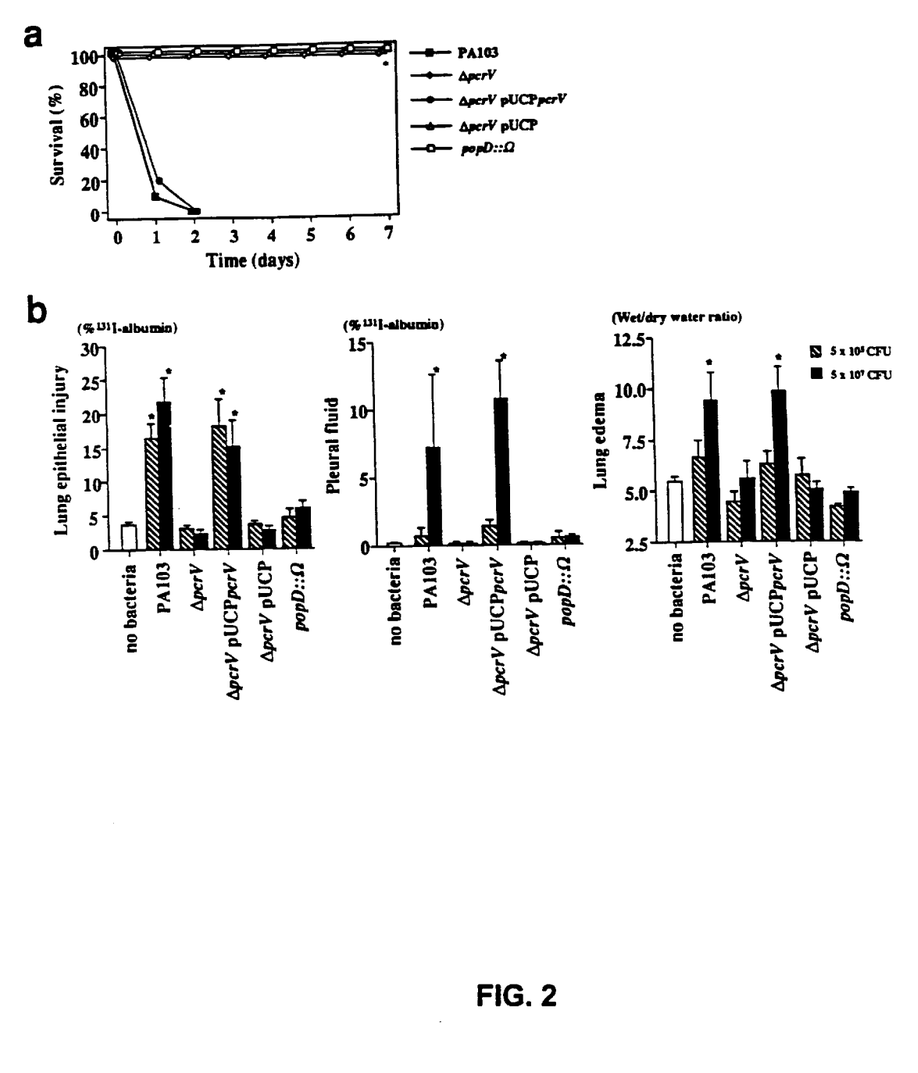
FIGS. 2A and 2B are a graph (FIG. 1A) and set of bar graphs (FIG. 2B) illustrating the survival and lung injury of *P. aeruginosa* parental and mutant strains.

Wild-type and mutant *P. aeruginosa* strains were tested in an acute lung infection model using low and high challenge doses of bacteria. Survival measurements indicated that PcrV and PopD were required to induce a lethal infection (FIG. 2A). In experiments utilizing three independent measurements of lung injury (the flux of labeled albumin from the airspaces of the lung to the bloodstream, the flux of labeled albumin from the airspaces of the lung to the pleural fluids, and the wet/dry ratio, which measures lung edema) the degree of injury caused by PA103ΔpcrV, the vector control strain (PA103ΔpcrVpUCP18), and PA103 popD::Ω were no different than the uninfected control animals (FIG. 2B). Complementation of PA103ΔpcrV with pcrv in trans restored lung injury levels to those measured with the parental strain, PA103. Taken together these data indicate that PcrV expression is required for virulence of *P. aeruginosa* in the acute lung infection model and that part of the function of PcrV appears to be linked to the ability to translocate type III effector proteins into eukaryotic cells.

FIGS. 2A and 2B are a graph (FIG. 2A) and set of bar graphs (FIG. 2B) illustrating the survival and lung injury of *P. aeruginosa* parental and mutant strains. Referring to FIG. 2A, mice were challenged with $5\times10^5$ cfu of each of the indicated strains and survival was monitored for one week. Referring to FIG. 2B, lung injury was assessed by the flux of labeled albumin from the airspaces of the lung to the blood (lung epithelial injury), to the pleural fluid (pleural fluid) or by measuring the wet/dry ratio (lung edema). Two bacterial infectious doses were used as denoted by the solid and striped bars. Significant differences (*p<0.001) between control and test groups was determined by one-way ANOVA and Dunnet multiple comparison tests. The following abbreviations were used: PA103, parental wild-type strain; ΔpcrV, PA103ΔpcrV; ΔpcrVpUCPpcrV, PA103ΔpcrV complemented with a plasmid expressing PcrV; ΔpcrVpUCP, PA103ΔpcrV with a vector control; popD::Ω, PA103popD::Ω, a translocation defective strain.

2. Immunization with PcrV

Figure 3:
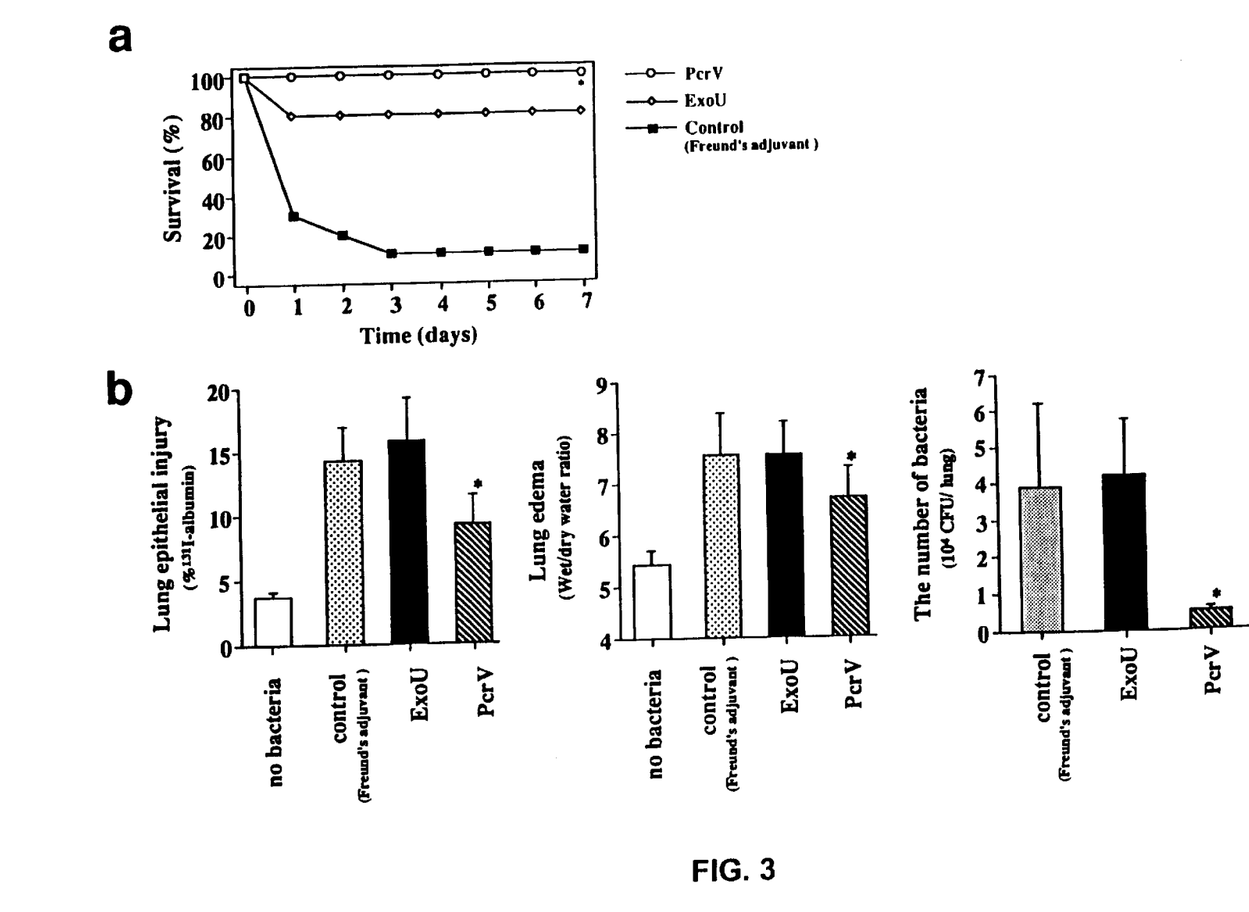
FIGS. 3A and 3B are a graph (FIG. 3A) and a set of bar graphs (FIG. 3B) illustrating the effect of immunization on survival, lung injury, and bacterial colonization.

To determine whether immunization with PcrV protected animals from a lethal lung infection, recombinant PcrV (rPcrV) or ExoU (rExoU) were purified as histidine-tagged fusion proteins and used as antigens. Mice were immunized and subsequently challenged via their airspaces with a lethal dose of strain PA103. When survival was measured, both vaccines protected the mice (FIG. 3A). When lung injury was assessed, only PcrV vaccinated animals had significantly less epithelial damage and lung edema (FIG. 3B). Animals immunized with the PcrV vaccine also had significantly fewer bacteria in their lungs, suggesting that a blockade of the *Pseudomonas* V antigen may facilitate rapid clearance of bacteria from the lung, protecting the animals from severe epithelial injury (FIG. 3B).

FIGS. 3A and 3B are a graph (FIG. 3A) and a set of bar graphs (FIG. 3B) illustrating the effect of immunization on survival, lung injury, and bacterial colonization. Referring to FIG. 3A, mice were immunized (PcrV, n=10; ExoU, n=5; control, n=10) as indicated and challenged with strain PA103 at $5\times10^5$ CFU/animal. The percent of surviving animals was determined for one week; p<0.05 by the Mantel-Cox log rank test. Referring to FIG. 3B, lung injury assessment and bacterial colonization of vaccinated animals 4 hours after installation of PA103. Lung epithelial injury, lung edema, and bacterial burden; PcrV, n=9; ExoU, n=4; and control, n=8. The final number of bacteria in the lung is indicated as the number on the Y axis×$10^4$ CFU. Significant differences (*) for lung injury (p<0.01), lung edema (p<0.05), and bacterial numbers (p<0.05) as determined by Dunnet multiple comparison test. One-way ANOVA for lung injury, p=0.0005; lung edema, p=0.0437; bacterial burden, p=0.0075.

Figure 4:
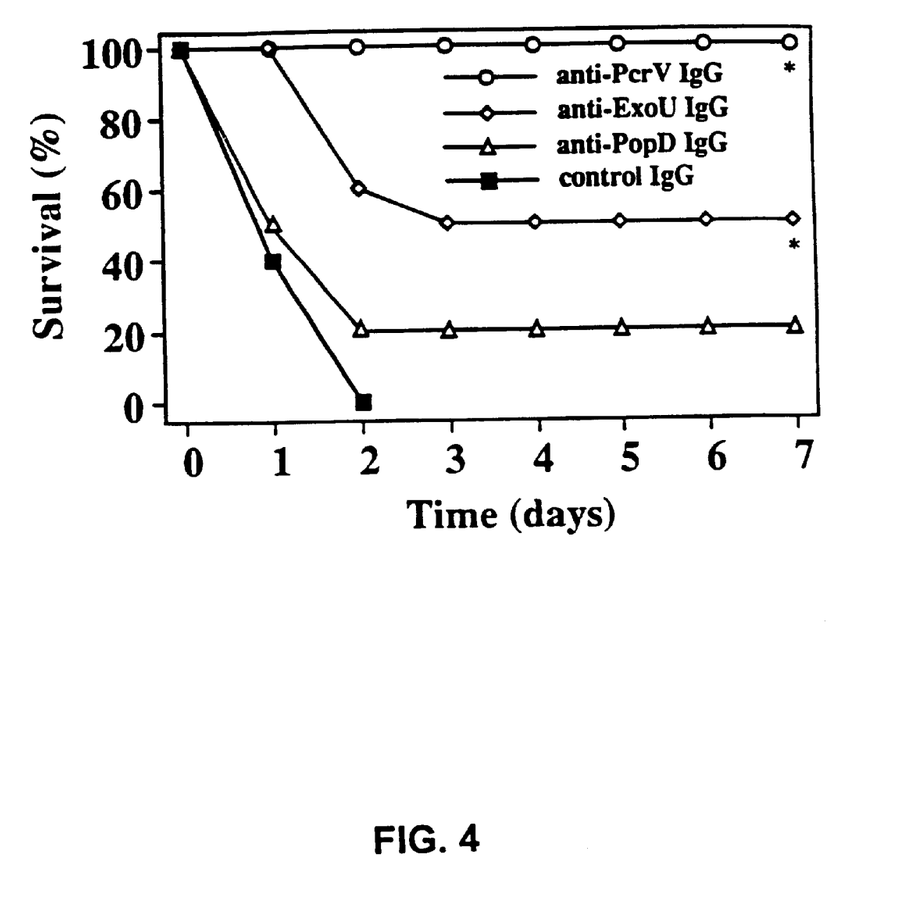
FIG. 4 is a graph of the number of animals surviving a challenge with $5 \times 10^5$ CFU/mouse of strain PA103 after passive administration of polyclonal IgG specific for PcrV, ExoU, PopD or control IgG from an unimmunized animal.

To determine whether therapeutic intervention was possible, mice were passively immunized with preimmune rabbit IgG or rabbit IgG specific for rPcrV, rExoU, or rPopD one hour prior to airspace instillation of PA103 at a concentration of $5\times10^5$ CFU/mouse. Antibodies to rPcrV provided complete protection to a lethal infection (FIG. 4). Anti-rExoU IgG provided partial survival, which was significantly different from the administration of control IgG, although all the surviving animals appeared severely ill during the trial. Survival was not improved by the passive transfer of antibodies to another of the type III translocation proteins, PopD. From these results we conclude that antibodies to PcrV are highly protective in the acute lung infection model and that PcrV may be exposed on the bacterial surface or in a soluble form that is available for antibody-antigen interactions.

FIG. 4 is a graph of the number of animals surviving a challenge with $5\times10^5$ CFU/mouse of strain PA103. Animals were pretreated with 100 μg of immune IgG or control IgG from an unimmunized rabbit (rPcrV, preimmune serum). N=10 for each group; *p<0.05 versus control group for treatment with anti-PcrV and anti-ExoU IgG preparations by Mantel-Cox log rank test.

If PcrV is accessible for neutralization, then concomitant administration of the bacterial inoculum with anti-rPcrV IgG should completely protect against lung injury and lethality. IgG preparations were mixed with the inoculum (10-fold higher dose than the lethal inoculum) prior to instillation of the bacteria into the lung and survival was measured. Only anti-rPcrV IgG was protective against this extreme infection (FIG. 5A). Lung injury was measured in animals infected with the normal lethal dose of $5 \times 10^5$ bacteria. The efflux of labeled albumin from the airspaces of the lung was only 3% more than uninfected controls (FIG. 5B) after co-administration of anti-rPcrV IgG. The decreased efflux of labeled protein from the lung to the pleural fluids was the same as the uninfected controls when anti-PcrV was included with the inoculum. Curiously lung edema, as measured by the wet/dry ratio, was significantly reduced by the addition of either anti-rPcrV or anti-rPopD. (FIG. 5B). Thus, the concomitant administration of anti-rPcrV IgG with the bacteria was even more effective in normalizing all the lung injury parameters than vaccination. These data support the accessibility of PcrV for antibody-mediated neutralization and document a clinically relevant decrease in lung injury; antibodies to PcrV may serve as therapeutic reagents in the treatment of severe nosocomial pneumonia caused by *Pseudomonas aeruginosa*.

Figure 5:
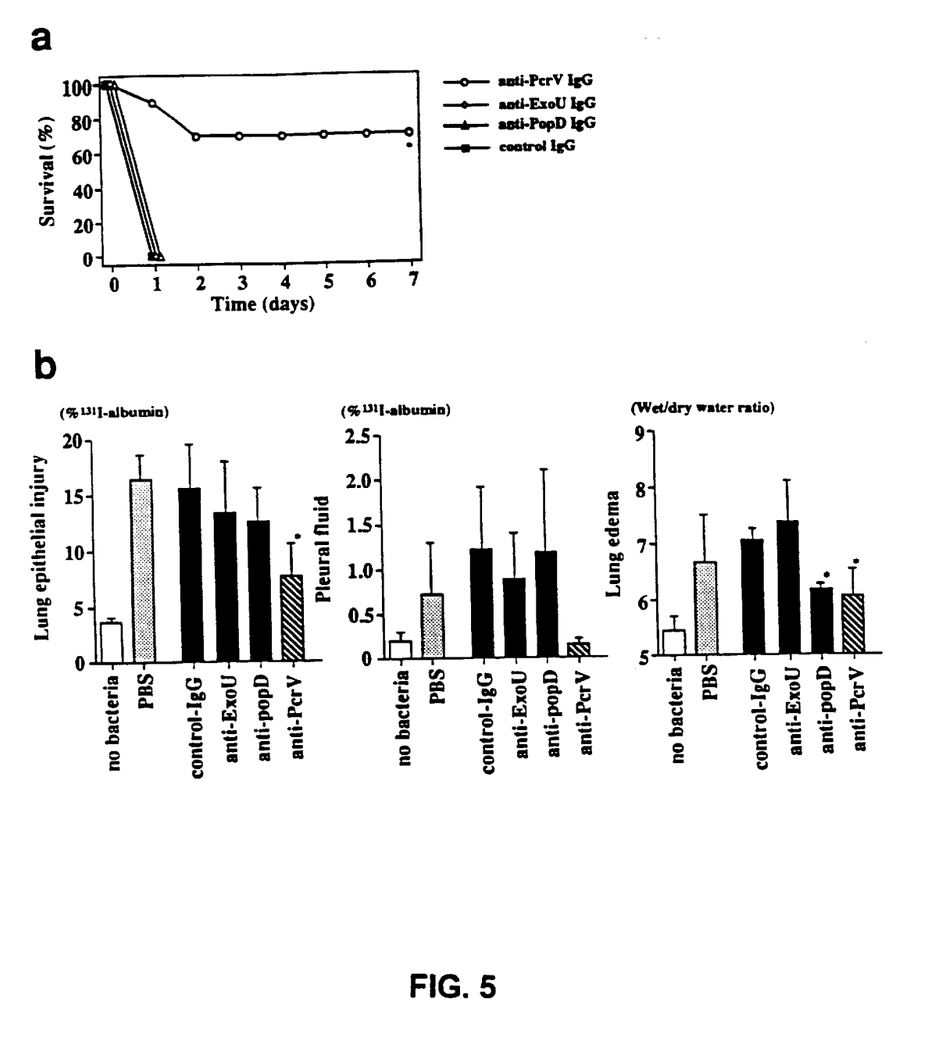
FIGS. 5A and 5B are a graph (FIG. 5A) and a set of bar graphs (FIG. 5B) illustrating survival and protection from lung injury by concomitant administration of IgG to different bacterial antigens and bacterial challenge. One-way ANOVA for lung injury, p=0.026, and lung edema, p<0.0005.

FIG. 5 is a graph (FIG. 5A) and a set of bar graphs (FIG. 5B) illustrating survival and protection from lung injury by concomitant administration of IgG and bacterial challenge. IgG (5 μg) was mixed with either $5 \times 10^6$ (for survival assays, n=10 per group) or $5 \times 10^5$ (for the measurement of lung injury, n=4 to 6 animals per group) *P. aeruginosa* strain PA103. This mixture was instilled into the lungs and survival (FIG. 5A) or lung injury (FIG. 5B) was assessed. For survival, *p<0.05 versus control IgG for anti-PcrV by the Mantel-Cox log rank test; for lung epithelial injury and lung edema *p<0.05 versus control IgG by Dunnet multiple comparison test. One-way ANOVA for lung injury, p=0.026, and lung edema, p<0.0005.

In acute *P. aeruginosa* infections, the net effect of type III-mediated intoxication may be to promote the dissemination of the bacterium beyond the epithelium leading to infection of the pleural fluids, spleen, liver, and bloodstream. Bloodborne infections with *P. aeruginosa* from either acute ventilator-associated pneumonia or from burn wound infections can result in a 40–80% mortality rate in spite of aggressive antibiotic treatment (16). PcrV must be a component of the type III translocation complex in *P. aeruginosa*, as mutants defective in the production of this protein are unable to intoxicate CHO cells or cause lung epithelial injury even though they are able to produce and secrete the type III effectors and proteins required for translocation. Unlike PopD, which is also necessary for translocation, PcrV is accessible for antibody-mediated neutralization suggesting that antibodies may be useful therapeutic agents in acute infections.

3. Methods for Examples 1 and 2

Construction of a Nonpolar Insertion in PcrV and Complementation.

A 5.0-kb EcoRI-NsiI restriction fragment encoding pcrGVHpopBD and flanking sequences was cloned into the allelic replacement vector pNOT19 (17). Two NotI sites (one within pcrG and one within popB) were removed from the inserted sequences by using the Sculptor mutagenesis system (Amersham). An internal SstI restriction fragment was deleted from pcrv, resulting in an in-frame deletion of residues 17–221 (pNOTΔpcrV). To select for integration of the plasmid, a gene encoding tetracycline resistance (TcΩ) was cloned into the HindIII site of the vector (pNOTΩΔpcrV). The MOB cassette (17) was added as a NotI fragment. Selection of merodiploids, resolution of plasmid sequences, and confirmation of allelic replacement was performed as previously described (18). A shuttle plasmid (pUCP, 19) was used to construct a clone to complement the pcrv deletion. The coding sequence for PcrV was amplified and cloned behind the control of the ExoS promoter region (20). The transcription of ExoS is coordinately regulated with the operons that control type III secretion and translocation in *P. aeruginosa* (2). The nucleotide sequence was confirmed for each DNA construct involving site specific mutagenesis, PCR amplification, or in-frame deletion.

SDS-PAGE and Western Blot Analysis of Secreted Products.

*P. aeruginosa* were grown under inducing (+NTA) or non-inducing conditions (−NTA) for expression of the type III secreted products (18). Cultures were harvested based on optical density measurements at 540 nm and supernatant fractions were concentrated by the addition of a saturated solution of ammonium sulfate to a final concentration of 55%. Each lane of an SDS-polyacrylamide gel (11%) was loaded with 3 μl of a 20-fold concentrated supernatant and stained with Coomassie blue. An identical gel was subjected to Western blot analysis as previously described (3–5) using a cocktail of rabbit antisera, which specifically recognizes ExoU, PopD, and PcrV. Protein A labeled with $^{125}I$ was used as a secondary reagent to identify bound IgG.

Infection Models and Lund Injury Assessments.

Chinese Hamster Ovary cells (CHO) were used in an in vitro infection model designed to measure cytotoxicity and type III translocation (21). Briefly, a bacterial inoculum was prepared in tissue culture medium without serum. CHO cells, which were propagated in serum containing medium, were washed and infected with various *P. aeruginosa* strains at a multiplicity of infection of 5:1. Cultures were incubated under tissue culture conditions for 3 hours (37° C., 5% $CO_2$), washed, and stained with trypan blue. Permeability to the dye was determined from phase contrast photographs. Infection with the parental strain PA103, which expresses ExoU, results in trypan blue staining of approximately 80% of the monolayer after 3 hours of incubation and complete destruction of the monolayer at 4–5 hours of incubation. Mouse infections and assessment of lung injury was performed as previously described (16). Briefly, male 8 to 12-week old pathogen-free BALB/c mice were purchased from Simonsen Laboratories (Gilroy, Calif.) and housed in barrier conditions. The mice were briefly anesthetized with inhaled Metofane (methoxyflurane, Pitman-Moore, Mundelein, Ill.) and placed supine, at an angle of approximately 30°. Fifty microliters of the bacterial inoculum was instilled slowly into the left lobe using a modified 24 gauge animal feeding needle (Popper & Sons, Inc., New Hyde Park, N.Y.) inserted into the trachea via the oropharynx. When lung injury assessments were measured, 0.5 μCi of $^{131}I$-labeled human serum albumin (Merck-Frosst, Quebec, Canada), 0.05 μg of anhydrous Evans blue in ml of Ringer's lactate with 5% mouse albumin were added to the instillate. After 4 hours of infection, the mice were anesthetized, blood was collected by a carotid arterial puncture and median sternotomies were performed. The lungs, pleural fluids, tracheas, oropharynxes, stomachs, and livers were harvested, and the radioactivity was measured. The percentage of radioactive albumin that left the instilled lungs and entered the circulation or the pleural fluid was calculated by multiplying the counts measured in the terminal blood samples (per ml) times the blood volume (body weight×0.07). The wet-dry ratios of the lungs were determined by adding 1 ml of water to the lungs and homogenizing the mixture. Homogenates were placed in preweighed aluminum pans and dried to constant weight in an 80° C. oven for three days. Lung homogenates were also sequentially diluted and plated on sheep blood agar for quantitative assessment of bacteria.

Production of Rabbit Antiserum to PcrV, PopD, and ExoU.

rPcrV, rPopD, and rExoU were produced as histidine tagged fusion proteins in pET16b and purified by nickel chromatography as previously described (22). Rabbits were injected intradermally (10 sites) with 300 µg of recombinant protein emulsified in Freund's complete adjuvant, boosted with antigen in Freund's incomplete adjuvant, and periodically bled at 7 day intervals. For passive immunization, the IgG fraction was isolated using Protein A column chromatography (Pierce Chemicals, Rockford, Ill.). Mice were injected with 100 µg IgG (intraperitoneal injection) 1 hour before challenge with $5 \times 10^5$ CFU of strain PA103. For active immunization with rPcrV and rExoU, endotoxin was removed from protein preparations by extraction with 1% Triton X-114 (23). Following the extractions, Triton X-114 was removed by Sephacryl S-200 chromatography. All vaccine preparations contained less than 1 ng of endotoxin per 40 µg of recombinant protein as determined by using a limulus amebocyte lysate assay (BioWhittaker, Walkersville, Md.). BALB/c mice were injected subcutaneously with 10 µg of recombinant proteins in Freund's complete adjuvant. At day 30 the mice were boosted with an additional 10 µg of antigen in Freund's incomplete adjuvant. On day 51 the mice were challenged by instillation of *P. aeruginosa* into their left lungs.

4. Synthesis of Monoclonal Antibodies

Mice were immunized with 10 µg of purified, LPS-free, recombinant PcrV in Freund's complete adjuvant and boosted two weeks later with the same dose of antigen emulsified in Freund's incomplete adjuvant. Immunizations were performed subcutaneously. Spleens were harvested from mice one week after booster doses of PcrV in Freund's incomplete adjuvant.

A single spleen was placed in 5 ml of tissue culture medium without serum, cut into pieces and gently homogenized. Large pieces of tissue were allowed to settle from the homogenate and the supernatant, single-cell suspension was removed and subjected to centrifugation at 1200 rpm for 10 minutes. The pelleted cells were resuspended in 10 ml of a solution to lyse red blood cells for 5 minutes and subsequently underlaid with 10 ml of fetal bovine serum. The material was centrifuged at 1200 rpm for 8 minutes, the supernatant was discarded and the cells were suspended in 30 ml of medium.

Splenic cells and myeloma cells (P3×63Ag8.653) were harvested by centrifugation at 1200 rpm for 10 minutes, and each pellet was separately suspended in 10 ml of tissue culture medium. 108 spleen cells and $2 \times 10^7$ myeloma cells were mixed and pelleted together by centrifugation at 1200 rpm for 6 minutes. The supernatant was removed by aspiration and 1 ml of 35% polyethylene glycol (PEG) was added. The cells were suspended in this solution gently and centrifuged at 1000 rpm for 3 minutes. In some experiments centrifugation was eliminated.

Exactly 8 minutes after the addition of PEG, 25 ml of medium was added and the cells were gently resuspended. Following a 5 minute 1200 rpm centrifugation step, the cell pellet was suspended at a density of $1 \times 10^6$ per ml in 30% conditioned medium and 70% complete medium (with serum). The cells were incubated overnight at 37° C. The next day the cells were harvested by centrifugation and suspended in 200 ml of 30% conditioned medium and 70% complete medium with hypoxanthine, aminopterin and thymidine (HAT).

Approximately 0.2 ml of this cell suspension was added per well to ten 96-well plates (12 ml per 96 well plate). The density of the remaining cells was adjusted to $2.5 \times 10^5$ per ml and the cells were plated in the 96 well format. Plates were screened microscopically for single colonies and supernatants were subsequently tested for antibody production by enzyme-linked immunosorbent assay using recombinant PcrV as the antigen. Clones producing antibodies reactive to PcrV were subcultured to larger culture dishes and then isotyped.

The binding of antibodies was tested in an enzyme linked immunosorbent assay using recombinant PcrV as the antigen (histidine-tagged protein) coating the wells. Monoclonal antibodies were also tested in Western blot reactions using a *P. aeruginosa* supernatant containing native PcrV without the histidine tag.

4. References

1. Wiener-Kronish, J. P., Sawa, T., Kurahashi, K., Ohara, M., and Gropper, M. A., "Pulmonary edema associated with bacterial pneumonia," Pulmonary Edema (eds Matthay, M. A. and Ingbar, D. H.) pp. 247–267 (Marcel Dekker, Inc., New York, 1998).
2. Frank, D. W., "The exoenzyme S regulon of *Pseudomonas aeruginosa*," *Mol. Microbiol.* 26:621–629 (1997).
3. Finck-Barbancon, V., et al., "ExoU expression by *Pseudomonas aeruginosa* correlates with acute cytotoxicity and epithelial injury," *Mol. Microbiol.* 25:547–557 (1997).
4. Yahr, T. L., Goranson, J., and Frank, D. W., "Exoenzyme S of *Pseudomonas aeruginosa* is secreted by a type III pathway," *Mol. Microbiol.* 22:991–1003 (1996).
5. Yahr, T. L., Mende-Mueller, L. M., Friese, M. B., and Frank, D. W., "Identification of type III secreted products of the Pseudomonas aeruginosa exoenzyme S regulon," *J. Bacteriol.* 179:7165–7168 (1997).
6. Hueck, C. J., "Type III protein secretion systems in bacterial pathogens of animals and plants," *Microbiol. Mol. Biol. Rev.* 62:379–433 (1998).
7. Skrzypek, E. and Straley, S. C., "Differential effects of deletion in lcrV on secretion of V antigen, regulation of the low-$Ca^{2+}$ response, and virulence of Yersinia pestis," *J. Bacteriol.* 177:2530–2542 (1995).
8. Nakajima, R. and Brubaker, R. R., "Association between virulence of Yersinia pestis and suppression of gamma interferon and tumor necrosis factor alpha," *Infect. Immun.* 61:23–31 (1993).
9. Nakajima, R., Motin, V. L., and Brubaker, R. R., "Suppression of cytokines in mice by protein A–V antigen fusion peptide and restoration of synthesis by active immunization," *Infect. Immun.* 63:3021–3029 (1995).
10. Nedialkov, Y. A., Motin, V. L., and Brubaker, R. R., "Resistance to lipopolysaccharide mediated by the Yersinia pestis V antigen-polyhistidine fusion peptide: amplification of interleukin-10," *Infect. Immun.* 63:1196–1203 (1997).
11. Nilles, M. L., Fields, K. A., and Straley, S. C., "The V antigen of Yersinia pestis regulates Yop vectorial targeting as well as Yop secretion through effects on YopB and LcrG," *J. Bacteriol.* 180:3410–3420 (1998).

12. Kudoh, I., Wiener-Kronish, J. P., Hashimoto, S., Pittet, J. -F., and Frank, D. W., "Exoproduct secretions of *Pseudomonas aeruginosa* strains influence severity of alveolar epithelial injury," *Am. J. Physiol.* 267:L551–L556 (1994).
13. Apodaca, G., et al., "Characterization of Pseudomonas aeruginosa-induced MDCK cell injury: glycosylation-defective host cells are resistant to bacterial killing," *Infect. Immun.* 63:1541–1551 (1995).
14. Yahr, T. L., Vallis, A. J., Hancock, M. K., Barbieri, J. T., and Frank, D. W., "ExoY, a novel adenylate cyclase secreted by the Pseudomonas aeruginosa type III system," *Proc. Natl. Acad. Sci. USA*, in press (1998).
15. Finck-Barbancon, V., Yahr, T. L., and Frank, D. W., "Identification and characterization of SpcU, a chaperone required for efficient secretion of the ExoU cytotoxin," *J. Bacteriol.*, in press (1998).
16. Sawa, T., Corry, D. B., Gropper, M. A., Ohara, M., Kurahashi, K., and Wiener-Kronish, J. P., "IL-10 improves lung injury and survival in *Pseudomonas aeruginosa* pneumonia," *J. Immunol.* 159:2858–2866 (1997).
17. Schweizer, H. P., "Allelic exchange in *Pseudomonas aeruginosa* using novel ColE1-type vectors and a family of cassettes containing a portable orit and the counter-selectable *Bacillus subtilis* sacB marker," *Mol. Microbiol.* 6:1195–1204 (1992).
18. Frank, D. W., Nair, G., and Schweizer, H. P., "Construction and characterization of chromosomal insertional mutations of the *Pseudomonas aeruginosa* exoenzyme S trans-regulatory locus," *Infect. Immun.* 62:554–563 (1994).
19. Schweizer, H. P., "Escherichia-Pseudomonas shuttle vectors derived from pUC18/19," *Gene* 97:109–112 (1991).
20. Yahr, T. L., Hovey, A. K., Kulich, S. M., and Frank, D. W., "Transcriptional analysis of the *Pseudomonas aeruginosa* exoenzyme S structural gene," *J. Bacteriol.* 177:1169–1178 (1995).
21. Vallis, A. J., Yahr, T. L., Barbieri, J. T., and Frank, D. W., "Regulation of ExoS production by *Pseudomonas aeruginosa* in response to tissue culture conditions," *Infect. Immun.* submitted.
22. Yahr, T. L., Barbieri, J. T., and Frank, D. W., "Genetic relationship between the 53- and 49 kilodalton forms of exoenzyme S from *Pseudomonas aeruginosa,*" *J. Bacteriol.* 178:1412–1419 (1996).
23. Aidi, Y. and Pabst, M. J., "Removal of endotoxin from protein solutions by phase separation using Triton X-114," *J. Immunol. Methods* 132:191–195 (1990).

We claim:

1. A method of treating *Pseudomonas aeruginosa* infection comprising inoculating a patient with an effective amount of isolated PcrV protein from *Pseudomonas aeruginosa*, wherein the amount of protein is sufficient to show moderation or reduction of *Pseudomonas aeruginosa* infection as compared to control subjects.

2. The method of claim 1 wherein the patient is inoculated with recombinant PcrV protein.

3. The method of claim 1 wherein the patient is a human patient.

4. A method of treating a *Pseudomonas aeruginosa* infection comprising the step of inoculating a *Pseudomonas aeruginosa*-infected patient with an effective amount of isolated PcrV protein from *Pseudomonas aeruginosa*, wherein the amount of protein is sufficient to show moderation or reduction of *Pseudomonas aeruginosa* infection as compared to control subjects.

* * * * *